(12) United States Patent
Moravek et al.

(10) Patent No.: US 10,499,827 B2
(45) Date of Patent: Dec. 10, 2019

(54) SYSTEM AND METHOD FOR INTERPRETATION OF SIGNAL-TO-NOISE RATIOS DETECTED IN AN ARRAY OF ELECTRODES SENSORS IN TERMS OF PHYSICAL AND COGNITIVE STATE

(71) Applicant: HONEYWELL INTERNATIONAL INC., Morris Plains, NJ (US)

(72) Inventors: Zdenek Moravek, Brno (CZ); David Kunes, Tisnov (CZ); Lukas Maly, Zlinsky kraj (CZ)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 147 days.

(21) Appl. No.: 15/708,945

(22) Filed: Sep. 19, 2017

(65) Prior Publication Data
US 2019/0082986 A1    Mar. 21, 2019

(51) Int. Cl.
*A61B 5/00* (2006.01)
*A61B 5/044* (2006.01)
*A61B 5/0468* (2006.01)
*A61B 5/0408* (2006.01)
*A61B 5/18* (2006.01)

(52) U.S. Cl.
CPC .......... *A61B 5/044* (2013.01); *A61B 5/0408* (2013.01); *A61B 5/0468* (2013.01); *A61B 5/04085* (2013.01); *A61B 5/18* (2013.01); *A61B 5/7207* (2013.01); *A61B 5/7221* (2013.01); *A61B 2562/046* (2013.01)

(58) Field of Classification Search
CPC combination set(s) only.
See application file for complete search history.

(56) References Cited

U.S. PATENT DOCUMENTS 5,891,045 A    4/1999 Albrecht et al.
8,874,301 B1    10/2014 Rao et al.
(Continued)

FOREIGN PATENT DOCUMENTS

EP    1627597 A1    2/2006
EP    2783725 A1    10/2014
WO    2016/044933 A1    3/2016

OTHER PUBLICATIONS

Extended EP Search Report for Application No. 18192334.3 dated Jan. 15, 2019.
(Continued)

*Primary Examiner* — George Manuel
(74) *Attorney, Agent, or Firm* — Lorenz & Kopf, LLP

(57) ABSTRACT

A method and system are provided for measuring the cognitive state of an individual by combining analysis of 2 independent quantities derived from a single sensor. The method comprises placing an array of electrocardiogram (ECG) sensors in contact with the individual. The sensors continually measure the ECG voltages and signal-to-noise ratios from each ECG. A distance to sensor and pressure applied to sensor our calculated for each ECG sensor that corresponds to the ECG voltage and signal-to-noise ratio measurements from each respective ECG sensor. Next, a graphical distance and pressure map is generated based on the combined signal-to-noise ratios of the ECG sensors and continually analyzed to determine the cognitive state of the individual.

18 Claims, 6 Drawing Sheets

(56) References Cited

U.S. PATENT DOCUMENTS

| | | | |
|---|---|---|---|
| 2011/0087113 A1* | 4/2011 | Mack | A61B 5/024 600/481 |
| 2012/0265080 A1 | 10/2012 | Yu et al. | |
| 2017/0086699 A1 | 3/2017 | Shirai | |

OTHER PUBLICATIONS

Martinez, et al.; Heart and respiration unobtrusive sensors integrated in the vehicle; This work is funded by the European Union Seventh Framework Programme (FP7/2007-2013), under grant agreement No. 286265; Harken Project Website (http://harken.ibv.org/).

* cited by examiner

SYSTEM AND METHOD FOR INTERPRETATION OF SIGNAL-TO-NOISE RATIOS DETECTED IN AN ARRAY OF ELECTRODES SENSORS IN TERMS OF PHYSICAL AND COGNITIVE STATE

TECHNICAL FIELD

The present invention generally relates to biological parameters monitoring, and more particularly relates to a system and method for measuring the cognitive state of an individual.

BACKGROUND

Maintaining an alert cognitive state is obviously important for many jobs including aircraft pilots, vehicle drivers, etc. Various types of sensors and monitors exist to monitor individuals in these positions. However, these systems are often based on recording and analysis of a single type of bio-signal and hence are prone to partial or complete loss of function. Hence, there is a need for a system and method that measures the cognitive state of an individual based on several types of bio-signals that may be derived from readouts of a single sensor.

BRIEF SUMMARY

This summary is provided to describe select concepts in a simplified form that are further described in the Detailed Description. This summary is not intended to identify key or essential features of the claimed subject matter, nor is it intended to be used as an aid in determining the scope of the claimed subject matter.

A method is provided for measuring the cognitive state of an individual. The apparatus comprises: placing an array of electrocardiogram (ECG) sensors in contact with the individual; continually measuring the signal-to-noise ratio for each ECG sensor; calculating a distance and pressure between the individual and each ECG sensor that corresponds to the signal-to-noise ratio for each respective ECG sensor; generating a graphical distance and pressure map based on the combined signal-to-noise ratios of the ECG sensors; and continually analyzing the distance and pressure map to determine the cognitive state of the individual.

A system is provided for measuring the cognitive state of an individual. The system comprises: an array of electrocardiogram (ECG) sensors placed in contact with the individual, where the ECG sensors continually measuring the ECG voltage and related signal-to-noise ratio for each ECG sensor of the array; and a microprocessor that receives the signal-to-noise ratio from each ECG sensor, where the microprocessor, calculates a distance to each ECG sensor and pressure applied to each ECG sensor that corresponds to the ECG voltage and signal-to-noise ratio measurements, generates a graphical distance and pressure map based on the combined signal-to-noise ratios of the ECG sensors, and continually analyzes the distance and pressure map to determine the cognitive state of the individual.

Furthermore, other desirable features and characteristics of the system and method will become apparent from the subsequent detailed description and the appended claims, taken in conjunction with the accompanying drawings and the preceding background.

BRIEF DESCRIPTION OF THE DRAWINGS

The present invention will hereinafter be described in conjunction with the following drawing figures, wherein like numerals denote like elements, and wherein.

DETAILED DESCRIPTION

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

A system and method for measuring the cognitive state of an individual has been developed. One embodiment involves placing an array of capacitive electrocardiogram (ECG) sensors in indirect contact with a subject individual. The sensors continually measure the ECG voltage and determine the related signal-to-noise ratio for each sensor with the sensor hardware. Distance and pressure is calculated for each ECG sensor that corresponds to readout of the ECG voltage and its signal-to-noise ratio. Distance and pressure values that are calculated for each sensor of the array are used to generate a graphical distance and pressure map that is continually analyzed to determine the cognitive state of the individual.

Figure 1:
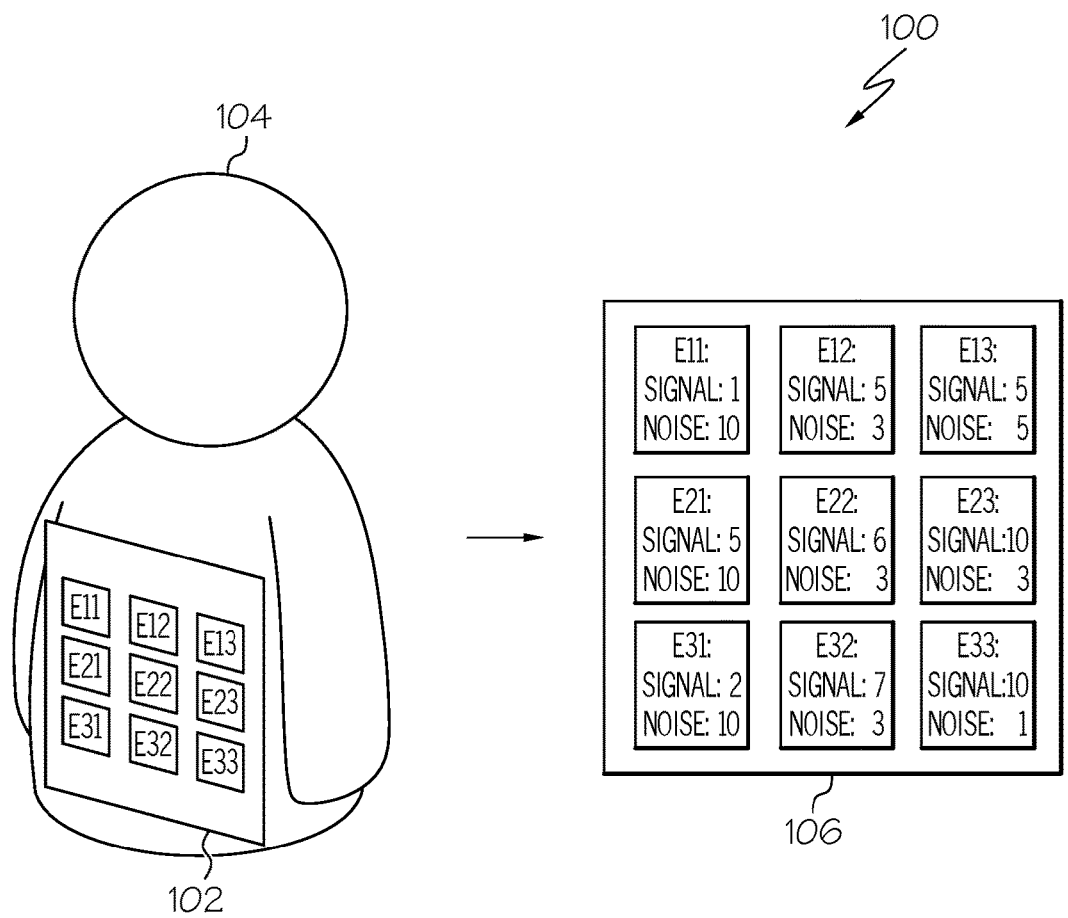
FIG. 1 shows a diagram of an array of electrocardiogram (ECG) sensors in physical contact with the subject individual in accordance with one embodiment.

Turning now to FIG. 1, a diagram 100 is shown of an array of electrocardiogram (ECG) sensors in contact with a subject individual 104 in accordance with one embodiment. In this example, a 3×3 square grid of ECG sensors 102 is shown. In alternative embodiments, the array of ECG sensors could be arranged in a rectangular or similar shaped grid pattern of sensors. Additionally, the grid pattern could be longer in the horizontal direction with a greater number of sensors in each horizontal row. This embodiment would have the advantage of providing more sensors in contact with the chest area of the subject individual 104.

The array collectively measures EC voltage and signal-to-noise ratio from each sensor recorded on the individual. In some embodiments, the contact with the skin of the individual is in direct because an ECG sensor may function with up to 1 centimeter (cm) of insulation between the individual and the sensor. This will account for any padding on the seat or clothing worn by the subject individual. In alternative embodiments, the sensors may be placed in direct physical contact with the individual.

A signal-to-noise ratio is determined by the hardware of each ECG sensor 106 as the strength of the signal divided by electronic background noise. In the embodiment shown, the sensor in the lower right-hand corner of the grid (E 33) is shown to have a relative signal strength of 10 with a relative noise strength of 1 for a signal-to-noise ratio of 10. This is the highest signal-to-noise ratio in the grid sensors and it reflects the strongest signal of the array. The strength of the signal is proportional to the distance between the individual and the sensor and to pressure applied on this sensor by the subject individual. Both distance and pressure are calculated for each sensor of the array.

Figure 2:
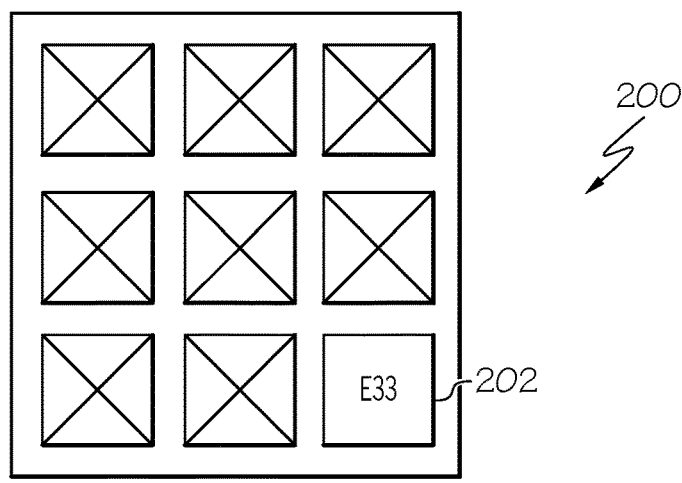
FIG. 2 shows a signal-to-noise ratio map of an ECG array in accordance with a prior art embodiment.
Figure 3:
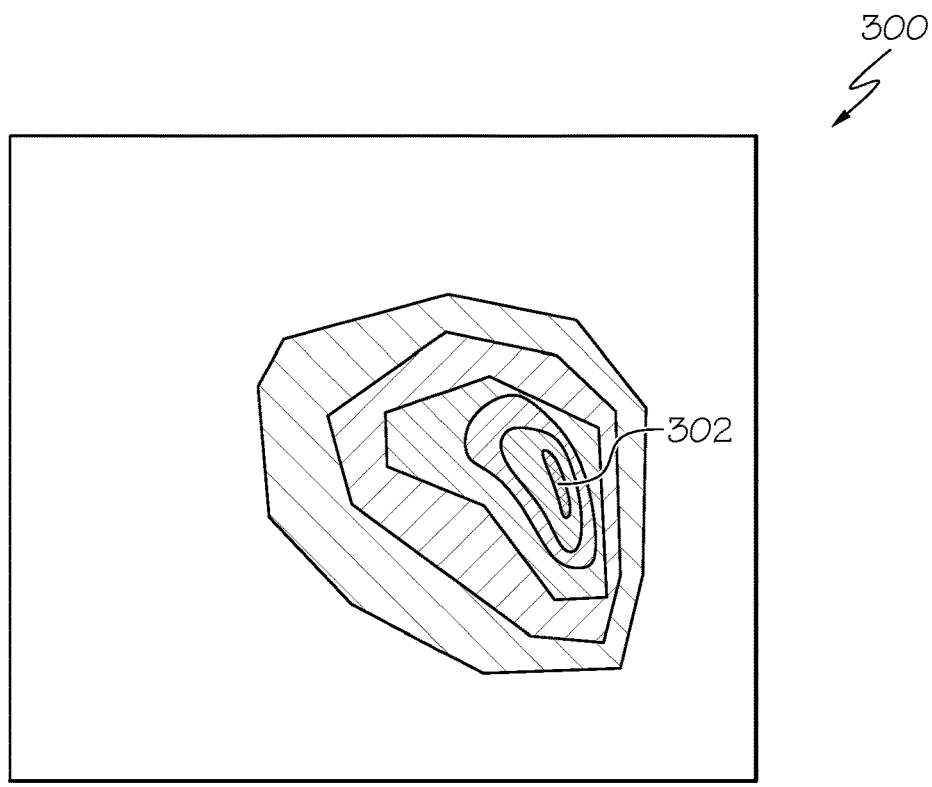
FIG. 3 shows a signal-to-noise ratio map of an ECG array in accordance with one embodiment.

Turning now to FIG. 2, a signal-to-noise ratio map 200 is shown of an ECG array in accordance with a prior art embodiment. In the prior art, the signal-to-noise ratio would merely identify E 33 sensor 202 as having the highest signal-to-noise ratio in the array. The signal from E 33 would be used to provide the most reliable ECG voltage of all sensors of the array while the signals from the other sensors in the array would be ignored. In contrast, FIG. 3 shows a signal-to-noise ratio map 300 of an ECG array in accordance with a present embodiment. In this embodiment, the signal-to-noise ratios 302 of each sensor are measured and reflected on the signal-to-noise ratio map with respect to quality of the contact. In this embodiment, color coding is used to indicate the relative value of the signal-to-noise ratios. In this manner, the signal-to-noise ratio map can provide a more complete mapping of the distance and pressure being applied on the sensor array. The map may then be used to determine the direction and extent of movement by the subject individual as an independent quantity together with the ECG voltage.

Figure 4:
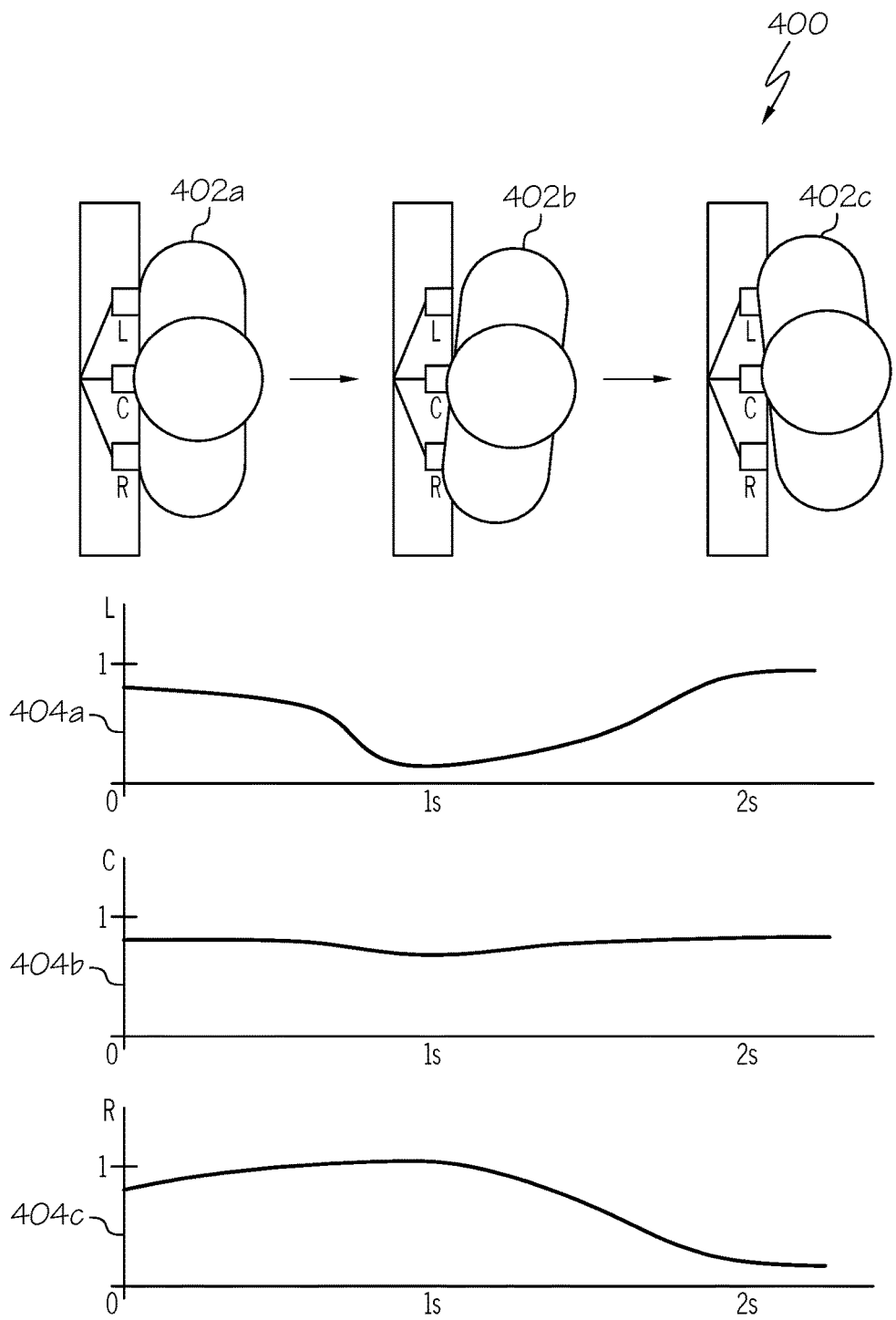
FIG. 4 shows signal-to-noise ratios of an ECG array corresponding to different subject individual physical positions in accordance with one embodiment.

Turning now to FIG. 4, a series of inputs to vertical columns of ECG sensors are shown in comparison to graphs of the output signal-to-noise ratios from those columns of sensors. Specifically, an overhead view is shown of a subject individual 402a, 402b and 402c in different positions while in contact with the left (L), center (C) and right (R) columns of the sensor array. Graphs of the signal-to-noise output for each column 404a, 404b and 404c are shown below the corresponding position of the subject individual. As shown, when the subject individual is in a normal position 402a, the signal-to-noise ratio on all columns of sensors is steady 404a, 404b, and 404c. As a subject individual shifts position to the right and increases pressure on the right side column of the array 402b, the signal-to-noise ratio increases 402c. Meanwhile, the signal-to-noise ratio decreases on the left side as the pressure decreases 404a. Conversely, as a subject individual shifts to the left side of the array and increases pressure there 402c, the signal-to-noise ratio increases on the left side column of sensors 404a. The signal-to-noise ratio decreases on the right side column of sensors as the pressure decreases 404c. It should be understood, that similar signal to noise ratio patterns can be achieved with other types of movement by the subject individual such as bending forward to increase the pressure on the bottom rows of the array and leaning back to increase pressure on the top rows of the array.

Figure 5:
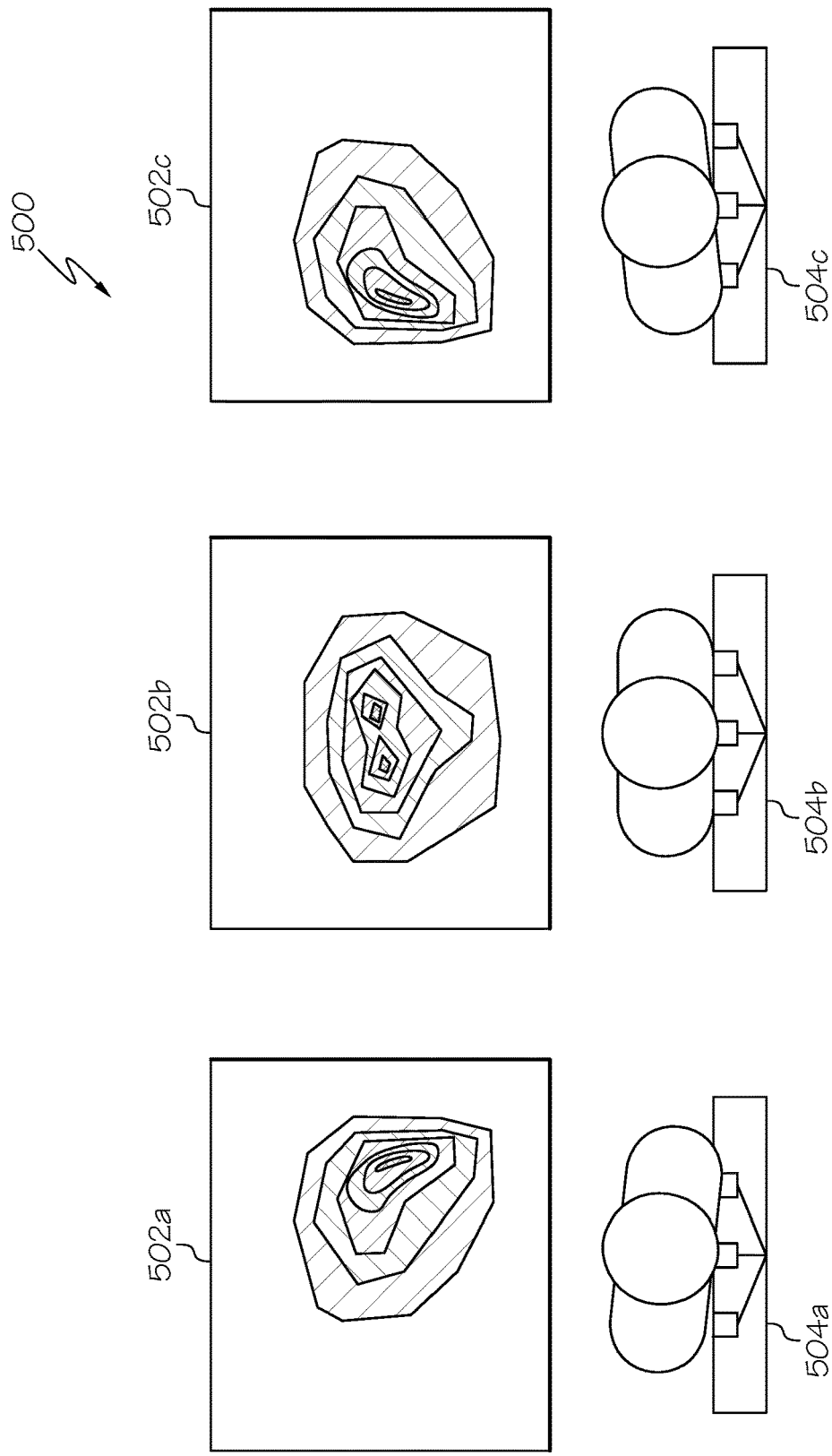
FIG. 5 shows signal-to-noise ratio maps of an ECG array corresponding to different subject individual physical positions in accordance with one embodiment.

Turning now to FIG. 5, a series of signal-to-noise ratio maps 500 are shown in comparison to the position of the subject individual. A signal-to-noise ratio map 502a representing the distance and pressure of the individual shifting to the right 504a is shown with a pattern that reflects higher signal-to-noise ratios on the right side of the array. Conversely, a signal-to-noise ratio map 502c representing the distance and pressure of the individual shifting to the left 504c is shown with a pattern reflecting higher signal-to-noise ratios on the left side of the array. With the subject individual seated in a normal position 504b, the signal-to-noise ratio map 502b shows a broad signal-to-noise ratio across the center of the array. In these embodiments, the distance and pressure maps of the ECG signal-to-noise ratios may be used to measure the movement, posture, breathing pattern and pulse rate of the individual. The pulse rate of the subject intimate visual may be determined by measuring the delay between the "R-peak" and blood pressure (BP) wave of the signal of the ECG sensors.

Figure 6:
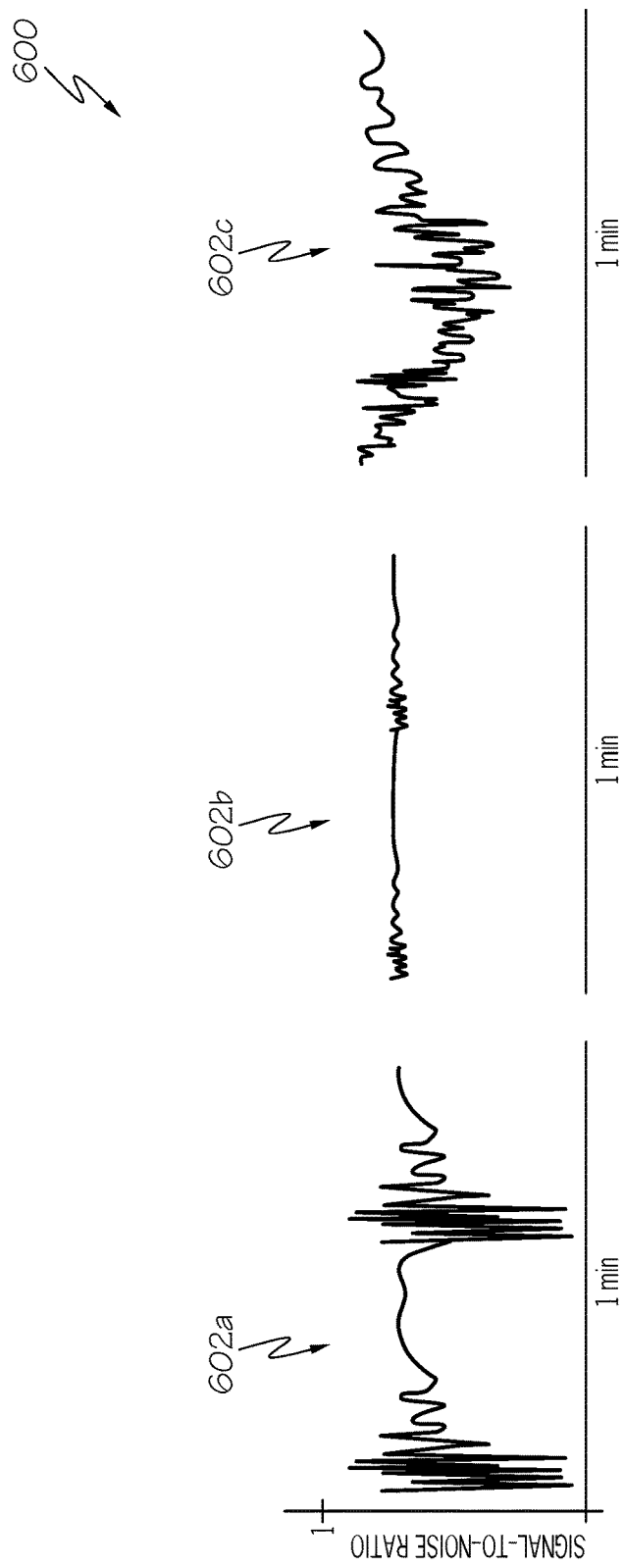
FIG. 6 shows graphs of ECG sensor signal-to-noise ratios corresponding to different cognitive states of a subject individual in accordance with one embodiment.

Turning now to FIG. 6, graphs of the ECG sensor signal-to-noise ratios 600 that correspond to different cognitive states of the subject individual are shown. These graphs 602a, 602b and 602c show signal-to-noise ratio outputs over the period of one minute. The first graph 602a shows high amplitude with repeated irregular patterns. This reflects wiggling by the subject individual and is one of the symptoms of fatigue, drowsiness or stress. If this is detected, an alarm may be sent to alert the individual. The second graph 602b shows low amplitude irregular patterns which are typical for small-scale body movements during low activity. This pattern indicates no fatigue and no alarm should be sent. The third graph 602c shows slow, high amplitude drift which reflects large-scale deliberate body movements during more demanding activity. This pattern also indicates no fatigue and no alarm should be sent. These examples demonstrate how continually monitoring the distance and pressure maps of the signal-to-noise ratios over a period of time may determine the cognitive state of the subject individual.

Figure 7:
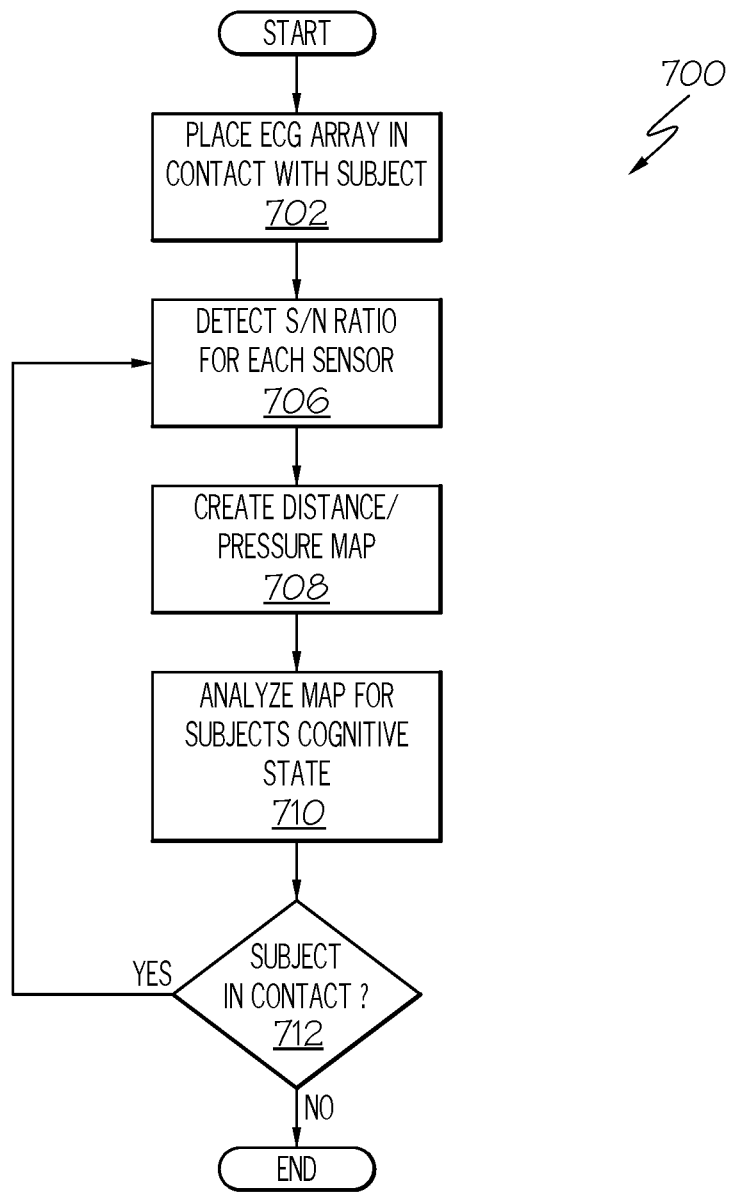
FIG. 7. shows a flowchart of a method of determining the cognitive state of an individual using signal-to-noise ratios from an ECG array in accordance with one embodiment.

Turning now to FIG. 7, a flowchart is shown of a method of determining the cognitive state of the individual using signal-to-noise ratios from an ECG array 700. First, the ECG array is placed in contact with the subject individual 702. The ECG sensors in the array are used to measure the ECG voltage and to generate a signal-to-noise ratio for each individual sensor 706. The signal-to-noise ratios are collectively used to create a distance and pressure signal map 708. The signal map is analyzed to determine the subject's cognitive state 710. The analysis continues as long as the subject is in contact with the sensor array 712. In various embodiments, this method may be used to monitor the cognitive state of aircraft flight crew, vehicle drivers, plant operators or any job requiring alertness of the subject individual.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for measuring the cognitive state of an individual, comprising:
   placing an array of electrocardiogram (ECG) sensors in contact with the individual;
   continually measuring the signal-to-noise ratio for each ECG sensor;
   calculating a distance and pressure between the individual and each ECG sensor that corresponds to the signal-to-noise ratio for each respective ECG sensor;
   generating a graphical distance and pressure map based on the combined signal-to-noise ratios of the ECG sensors, where the graphical distance and pressure map uses color coding to indicate relative values of the combined signal-to-noise ratios; and
   continually analyzing the distance and pressure map to detect high amplitude and repeated irregular patterns that indicate a fatigued cognitive state of the individual.

2. The method of claim 1, where the array of ECG sensors comprises a rectangular shaped grid pattern of sensors.

3. The method of claim 2, where the rectangular shaped grid pattern of sensors is longer in the horizontal direction.

4. The method of claim 3, where the array of ECG sensors is in physical contact near the chest of the individual.

5. The method of claim 1, where the array of ECG sensors comprises a 3×3 grid of sensors.

6. The method of claim 1, where contact comprises up to 1 centimeter (cm) of insulation between the individual and each ECG sensor.

7. The method of claim 1, where the calculated distance and pressure on each ECG sensor correspond to movement of the individual.

8. The method of claim 1, where the calculated distance and pressure on each ECG sensor correspond to posture of the individual.

9. The method of claim 1, where the calculated distance and pressure on each ECG sensor correspond to a breathing pattern of the individual.

10. The method of claim 1, where the calculated distance and pressure on each ECG sensor correspond to a pulse rate of the individual.

11. The method of claim 10, where the pulse arrival and transit times are determined by from the delay between the R-peak and blood pressure (BP) wave of the ECG signal.

12. The method of claim 1, where the distance and pressure map is generated based on combined amplitudes of the signal-to-noise ratios of the ECG sensors.

13. The method of claim 1, where the distance and pressure map is generated based on combined periodicity and chaotic descriptors of the signal to noise ratios of the ECG sensors.

14. The method of claim 1, where the distance and pressure map is generated based on combined speed of onset and decline of the signal-to-noise ratios of the ECG sensors.

15. A system for measuring the cognitive state of an individual, comprising:
   an array of electrocardiogram (ECG) sensors placed in contact with the individual, where the ECG sensors continually measuring the ECG voltage and related signal-to-noise ratio for each ECG sensor of the array; and a microprocessor that receives the signal-to-noise ratio from each ECG sensor, where the microprocessor, calculates a distance to each ECG sensor and pressure applied to each ECG sensor that corresponds to the ECG voltage and signal-to-noise ratio measurements, generates a graphical distance and pressure map based on the combined signal-to-noise ratios of the ECG sensors, where the graphical distance and pressure map uses color coding to indicate relative values of the combined signal-to-noise ratios, and continually analyzes the distance and pressure map to detect high amplitude and repeated irregular patterns that indicate a fatigued cognitive state of the individual.

16. The system of claim 15, where the individual is an aircraft pilot.

17. The system of claim 15, where the individual is a vehicle driver.

18. The system of claim 15, where the individual is a plant operator.

* * * * *